United States Patent
Silverman et al.

(10) Patent No.: US 7,624,953 B2
(45) Date of Patent: Dec. 1, 2009

(54) INFUSION STAND

(76) Inventors: Jeffrey M. Silverman, 1399 Central St., Stoughton, MA (US) 02072; Bradley S. Silverman, 210 East St., Foxboro, MA (US) 02035

( * ) Notice: Subject to any disclaimer, the term of this patent is extended or adjusted under 35 U.S.C. 154(b) by 570 days.

(21) Appl. No.: 11/445,532

(22) Filed: Jun. 3, 2006

(65) Prior Publication Data
US 2007/0221796 A1    Sep. 27, 2007

Related U.S. Application Data

(60) Provisional application No. 60/785,840, filed on Mar. 25, 2006.

(51) Int. Cl.
*A47F 5/00* (2006.01)
*A47K 1/04* (2006.01)

(52) U.S. Cl. .................. 248/125.1; 5/83.1; 5/86.1; 248/125.8; 248/129; 248/145.6

(58) Field of Classification Search .............. 248/125.1, 248/125.2, 125.8, 161, 121, 128–129, 145.6, 248/295.11; 5/83.1, 83.6, 86.1, 617–618, 5/620, 624
See application file for complete search history.

(56) References Cited

U.S. PATENT DOCUMENTS

| | | | |
|---|---|---|---|
| 589,806 A | 9/1897 | Bard | |
| 2,696,963 A | 12/1954 | Shepherd | |
| 3,014,682 A | 12/1961 | Veneman | |
| 3,822,051 A | 7/1974 | Karapita | |
| 3,914,808 A * | 10/1975 | Woods | ......................... 5/83.1 |
| 4,113,222 A | 9/1978 | Frinzel | |
| 4,332,378 A | 6/1982 | Pryor | |
| 4,635,492 A | 1/1987 | Vebelhart | |
| 4,725,027 A | 2/1988 | Bekanich | |
| 4,744,536 A | 5/1988 | Bancalari | |
| 4,797,050 A * | 1/1989 | Habicht | ....................... 414/420 |
| 4,832,294 A * | 5/1989 | Eidem | ...................... 248/125.8 |
| 4,892,279 A | 1/1990 | Lafferty et al. | |
| 4,901,967 A | 2/1990 | Petre | |
| 4,905,944 A | 3/1990 | Jost et al. | |

(Continued)

OTHER PUBLICATIONS

Easylift of America, Inc., Easylift Gas Springs, Catalog, Date Unknown, pp. 1-24, Melbourne, FL, U.S.A.

(Continued)

*Primary Examiner*—Amy J. Sterling
*Assistant Examiner*—Tan Le

(57) ABSTRACT

The present invention is directed to an infusion stand for supporting an articles such as an IV bag. In one embodiment, the infusion stand comprises a gas spring engaged with a moveable base assembly. The infusion stand further comprises a foot pedal assembly mounted to the base assembly that is adapted to actuate the gas spring. The infusion stand further comprises an extension arm having one end engaged with the gas spring and the other end to an IV bag support adapted to support one or more IV bags. The infusion stand may further comprise a handle assembly connected to the upper portion of the extension arm. In operation, depression of the foot pedal assembly causes activation of the gas spring which raises the IV bag support to a selected height. An operator may grasp the handle assembly to control upward or downward movement of the IV bag support to a desired height and fix the desired height by release of the foot pedal assembly.

11 Claims, 10 Drawing Sheets

U.S. PATENT DOCUMENTS

| | | |
|---|---|---|
| 5,078,349 A | 1/1992 | Smith |
| 5,110,076 A | 5/1992 | Snyder et al. |
| 5,112,019 A | 5/1992 | Metzler et al. |
| 5,135,191 A | 8/1992 | Schmuhl |
| 5,249,121 A | 9/1993 | Baum et al. |
| 5,319,816 A * | 6/1994 | Ruehl ............................. 5/600 |
| 5,417,246 A | 5/1995 | Perkins et al. |
| 5,433,409 A | 7/1995 | Knopp |
| 5,549,264 A | 8/1996 | West |
| 5,709,521 A * | 1/1998 | Glass et al. ................. 414/462 |
| 5,772,162 A | 6/1998 | Lin |
| 5,820,086 A | 10/1998 | Hoftman et al. |
| 5,924,658 A | 7/1999 | Shiery et al. |
| 6,056,249 A | 5/2000 | Fillon, Jr. |
| 6,251,113 B1 | 6/2001 | Appelbaum et al. |
| 6,430,761 B1 * | 8/2002 | Brandorff et al. ............. 5/86.1 |
| 6,431,505 B2 | 8/2002 | Chinn et al. |
| 6,581,913 B1 * | 6/2003 | Conomos et al. ........ 254/133 R |
| 6,626,445 B2 | 9/2003 | Murphy et al. |
| 6,840,484 B2 | 1/2005 | Jeon |
| 6,969,031 B2 * | 11/2005 | Ugent et al. ............. 248/125.8 |
| 7,168,665 B2 * | 1/2007 | Hong et al. ............... 248/125.1 |
| 7,296,960 B2 * | 11/2007 | Strong ........................ 414/546 |
| 2003/0106969 A1 | 6/2003 | Dillon et al. |
| 2007/0221796 A1 * | 9/2007 | Silverman et al. ........... 248/161 |
| 2009/0142172 A1 * | 6/2009 | Blankenship et al. .......... 5/658 |

OTHER PUBLICATIONS

Omni Med, Inc., Infusion I.V. Stands, On-Line Catalog (www.omnimed.com), 2005, pp. 30-33, Moorestown, NJ, U.S.A.

Alimed, Inc., On-Line Catalog (www.alimed.com), Date Unknown, Saf-T-Pole, SKU 931249 and 931250, 2 pages, Dedham, MA, U.S.A.

Allen Medical Systems, Inc., I.V. / Irrigation Tower—Lift Assist, On-Line Catalog (www.allenmedical.com), 2006, 2 pages, Acton, MA, U.S.A.

* cited by examiner

INFUSION STAND

CROSS-REFERENCE TO RELATED APPLICATIONS

This application claims priority to U.S. provisional patent application Ser. No. 60/785,840 filed on Mar. 25, 2006, which is hereby incorporated by reference in its entirety.

BACKGROUND OF THE INVENTION

Infusion stands or IV poles have been used for many years by the medical care industry as a means of supporting an IV bag which is used to provide an intravenous flow of a fluid to a patient. Depending upon the volume of fluid, IV bags can be heavy and the operator must lift and secure the IV bag to a hook support provided at the top of the IV pole. Such lifting actions may cause injury to the operator and/or the patient. In an attempt to solve this problem, conventional IV poles have employed a simple mechanical telescoping mechanism to raise the hook support. Although simple in design, such conventional IV poles have obvious drawbacks, including forcing the operator to physically lift and re-lock the pole carrying the hook support. Conventional IV poles or infusion stands have also been developed that raise the hook support by electro-mechanical, pneumatic, and/or hydraulic means powered by a battery or connected to an electrical outlet. Such conventional systems are expensive, require significant manufacturing, and are not simple to operate.

SUMMARY OF THE INVENTION

One object of the present invention is to provide an infusion stand that can be operated by a person in a simple manner to raise and/or lower one or more IV bags to a desired height.

Another object of the present invention is to provide an infusion stand that is stable in design throughout the raising and/or lowering of the IV bags.

Another object of the present invention is to provide an infusion stand that is significantly less expensive to manufacture than conventional devices.

The present invention is directed to an infusion stand for supporting an article such as an IV and/or irrigation bag. In one embodiment, the infusion stand comprises a gas spring engaged with a moveable base assembly. The infusion stand further comprises a foot pedal assembly mounted to the base assembly that is adapted to activate the gas spring. The infusion stand further comprises an extension arm having one end engaged with the gas spring and the other end to an IV bag support adapted to support one or more IV bags. The infusion stand may further comprise a handle assembly connected to the upper portion of the extension arm. In operation, depression of the foot pedal assembly causes activation of the gas spring which raises the IV bag support to a maximum predefined height if not resisted by the operator. Alternatively, an operator may grasp the handle assembly to control upward or downward movement of the IV bag support and may fix a selected height by release of the foot pedal assembly.

BRIEF DESCRIPTION OF THE DRAWINGS

The following description of the invention will be more fully understood with reference to the accompanying drawings in which.

DETAILED DESCRIPTION OF THE INVENTION

Figure 1:
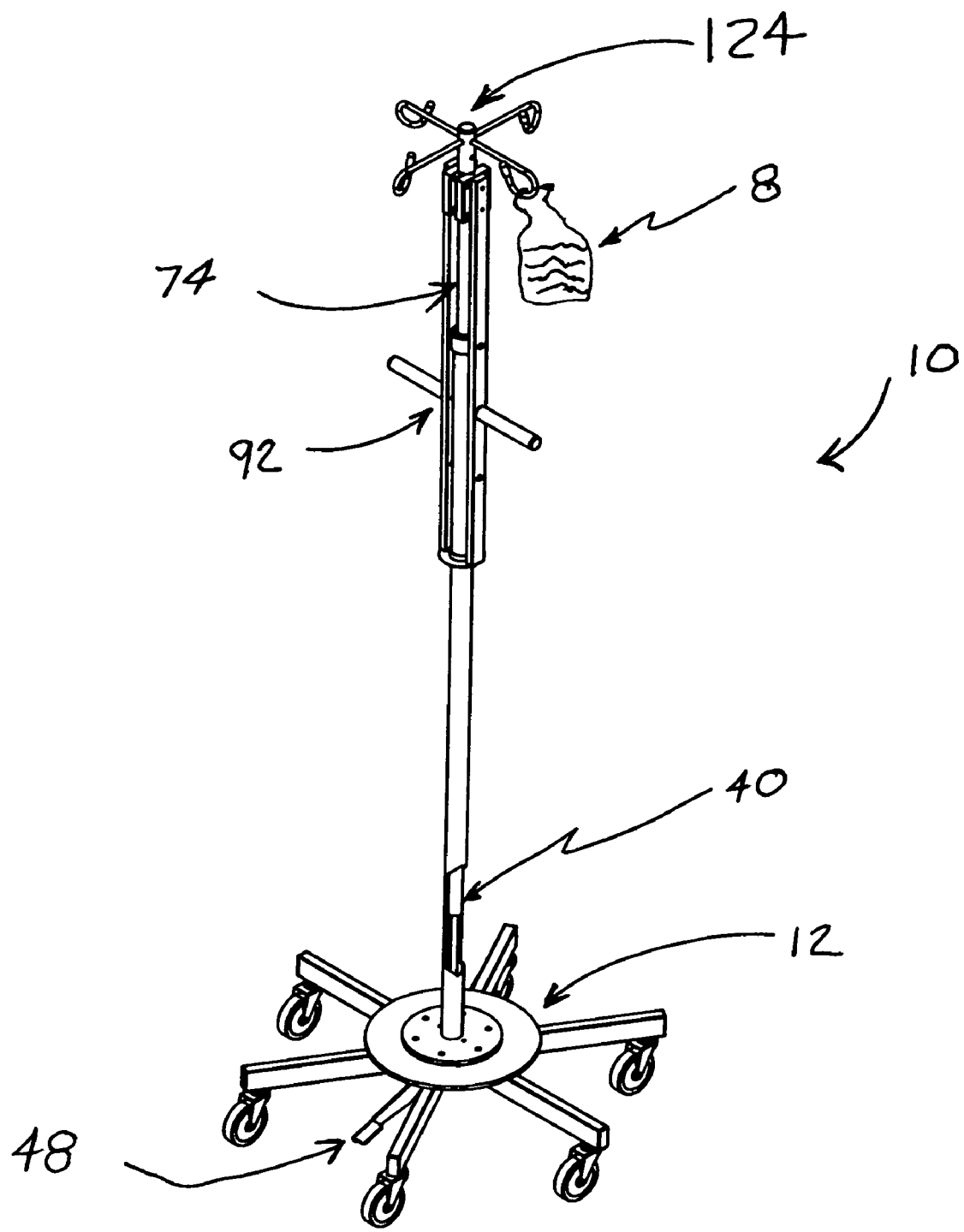
FIG. 1 is a perspective view of an infusion stand according to the present invention.
Figure 2B:
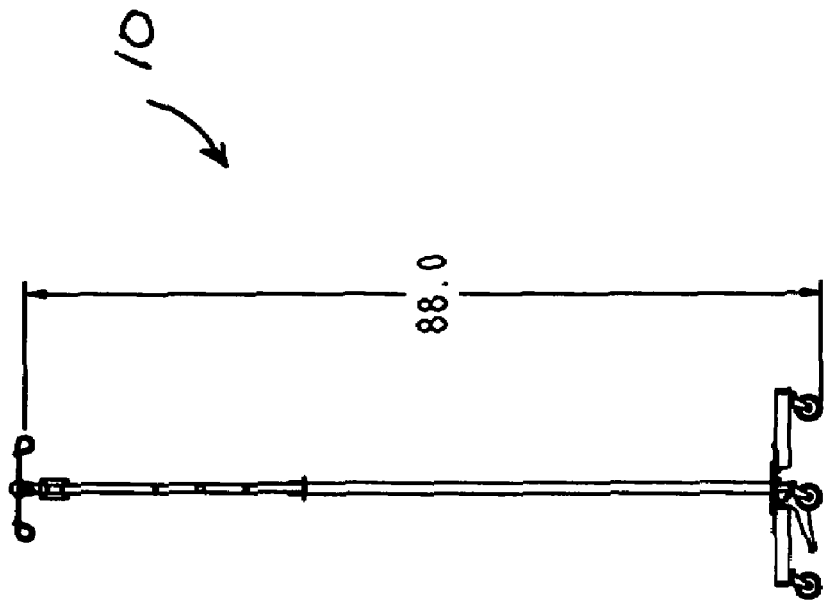
FIGS. 2A and 2B are elevation views of the infusion stand at different heights.
Figure 2A:
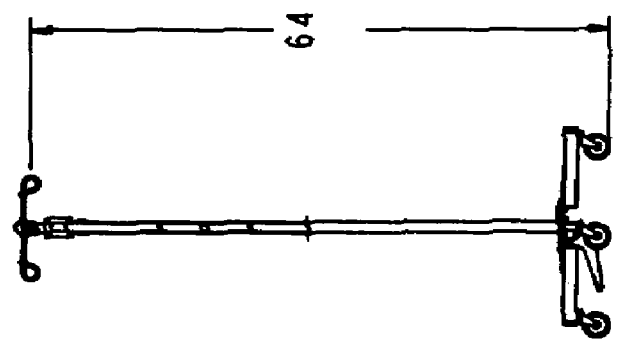

Referring to FIG. 1 and FIGS. 2A-2B, the present invention is a directed to an infusion stand 10 for supporting and selectively raising the height of an IV and/or irrigation bag 8. In one embodiment, infusion stand 10 generally comprises a gas spring 40 engaged with a moveable base assembly 12. Infusion stand 10 further comprises a foot pedal assembly 48 operatively engaged with gas spring 40. Infusion stand 10 further comprises an extension arm 74 connected to gas spring 40 and to an IV bag support 124 adapted to receive IV bag 8. Infusion stand 10 further comprises an outer post support 82 disposed substantially over gas spring 40 and extension arm 74. The infusion stand 40 further comprises a handle assembly 92 attached to extension arm 74. In operation, depression of foot pedal assembly 48 by an operator activates gas spring 40 which causes extension arm 74 and IV bag support 124 to be raised between a first height (FIG. 2A) and a second height (FIG. 2B). The operator may grasp handle assembly 92 to control upward or downward movement of IV bag support 124 and fix the desired height by release of foot pedal assembly 48.

Figure 3:
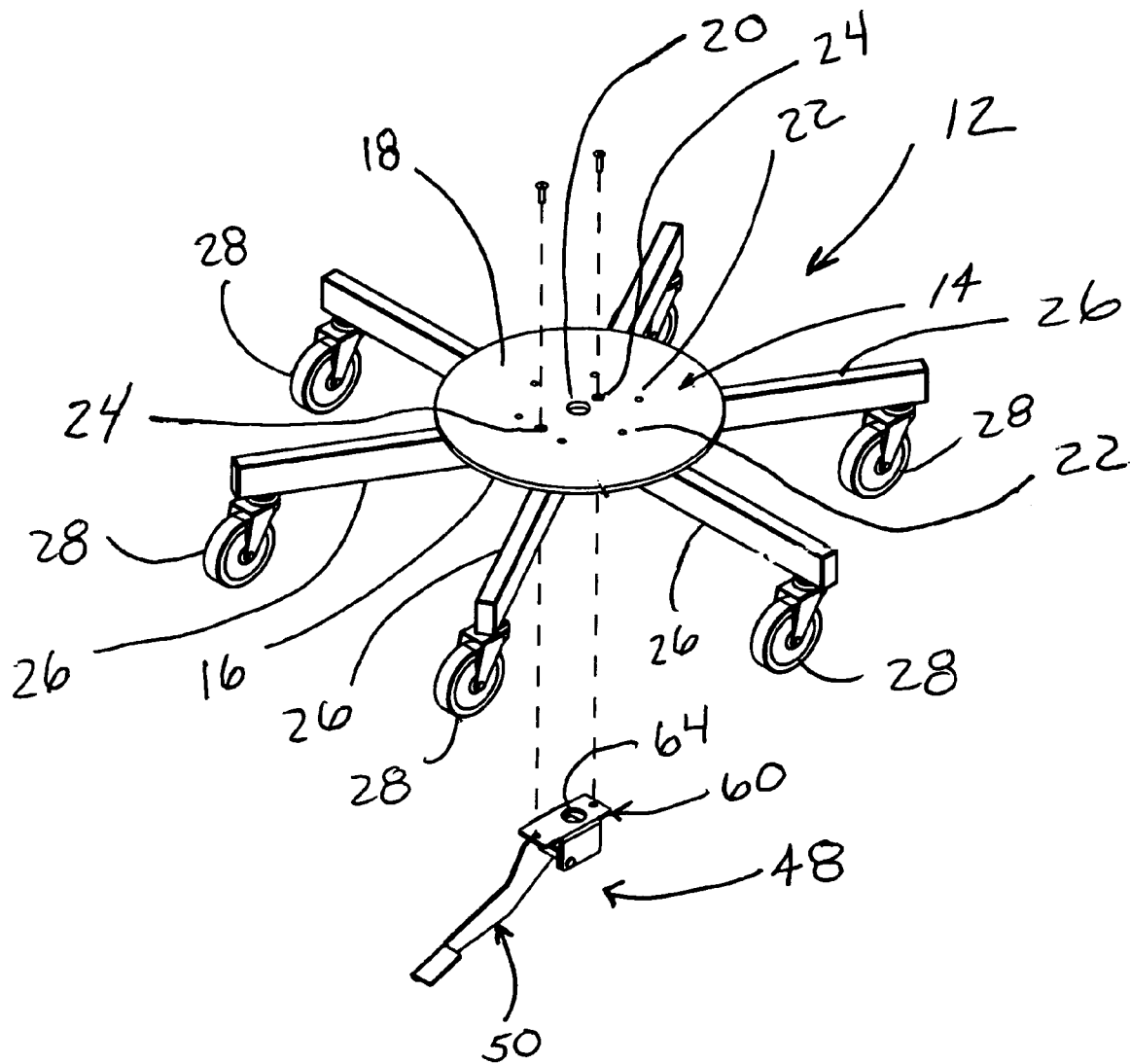
FIG. 3 is an exploded view of the base assembly and the foot pedal assembly.

Referring to FIG. 3, base assembly 12 generally comprises a base member 14 having a lower surface 16, an upper surface 18, a central opening 20, mounting holes 22, and mounting holes 24. In the embodiment shown, base member 14 takes the form of a circular plate and may be made from conventional materials such as steel and conventional processes. As will be described more fully herein, mounting holes 22 are provided as a means of securing the outer post support 82 to the base member 14. As will be described more fully herein, mounting holes 24 are provided as a means of securing the foot pedal assembly 48 to the base member 14. Base assembly 12 further comprises a plurality of legs 26 connected to the base member 14. Base assembly 14 further comprises a wheel 28 attached to each of legs 26 by conventional means. In the embodiment shown, wheels 28 are caster type wheels. Casters allow for easy movement of the stand from one location to another and one locking caster when activated prevents the infusion stand 10 from being moved inadvertently.

Figure 4:
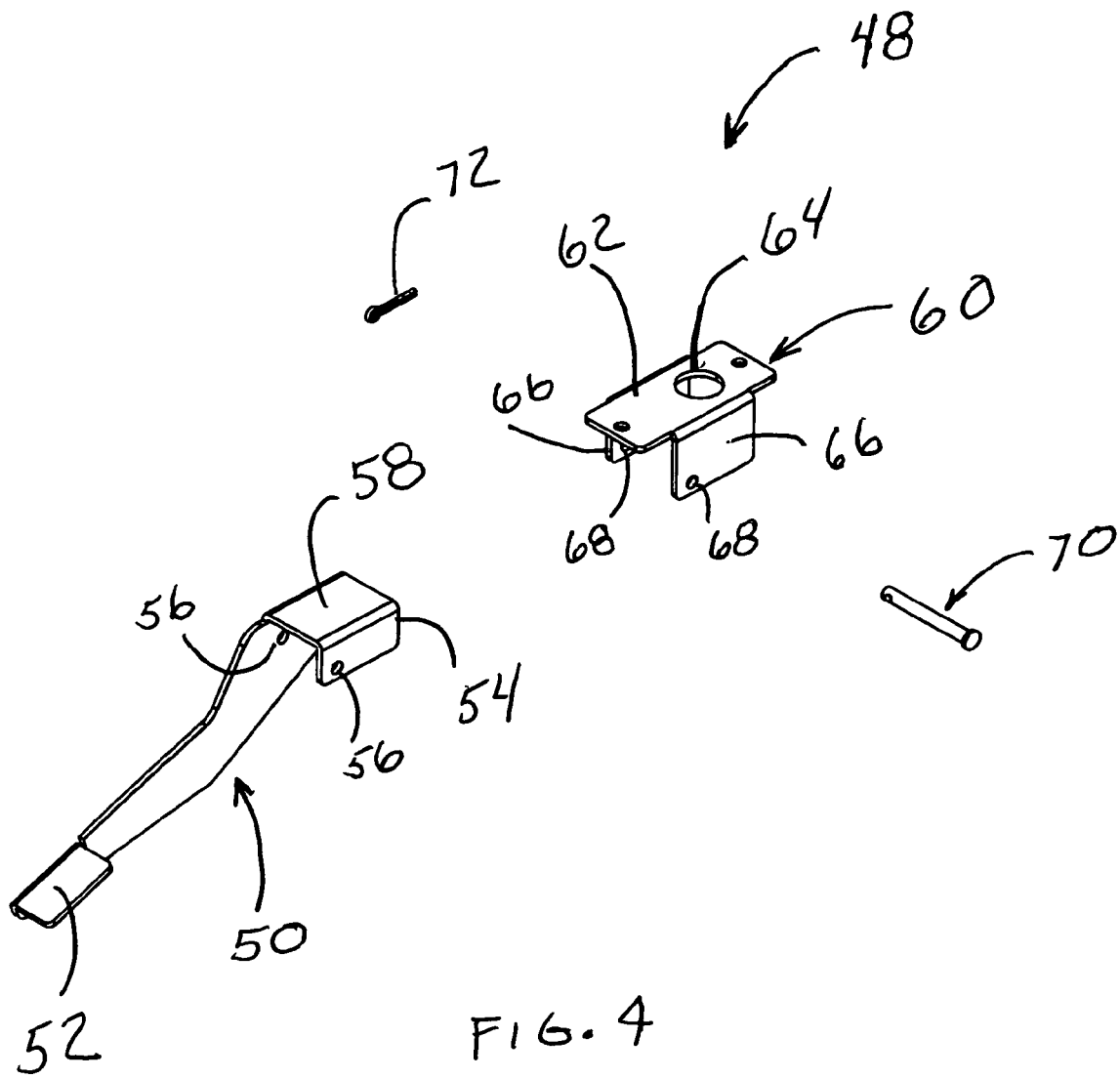
FIG. 4 is an exploded view of the foot pedal assembly.

Referring to FIGS. 3 and 4, foot pedal assembly 48 generally comprises a foot pedal 50 pivotally connected to a support bracket 60 about a clevis pin 70. Foot pedal 50 comprises a front portion 52 adapted to be depressed by an operator's foot and a rear portion 54. Rear portion comprises a pair of opposing openings 56 adapted to receive the clevis pin 70. Rear portion 52 further comprises an engagement surface 58 which as will be described more fully herein is adapted to engage with an activation pin 42 (to be described) of gas spring 40 when the front portion 52 is depressed. Support bracket 60 comprises an upper portion 62 having an opening 64 and sidewall portions 66 having openings 68. Openings 68 are adapted to receive clevis pin 70 which is secured by a cotter pin 72. Support bracket 60 is secured to the base member 14 by conventional means such that opening 64 is aligned with opening 20 of the base member 14.

Figure 5:
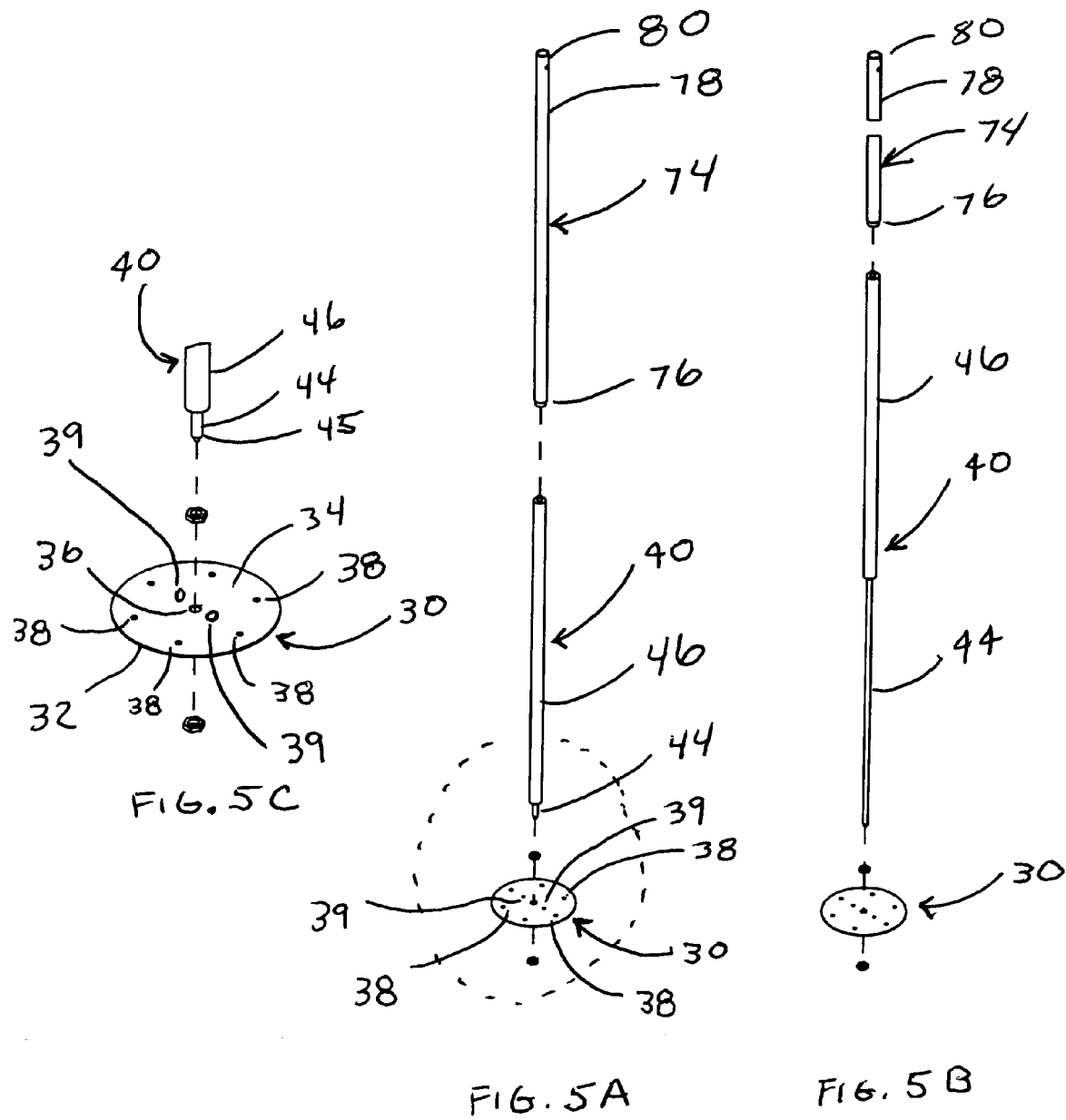
FIGS. 5A-5C are exploded views showing the assembly of the gas spring, extension arm, and support plate.

Referring to FIGS. 5A-5C, gas spring 40 is hereby defined as a self-contained unit that does not require any electricity or battery power, pneumatics, and/or hydraulics to operate it. Gas spring 40 comprises a piston portion 44, a pressurized cylinder portion 46, and an actuation pin 42 extending from an end portion 45 of the piston portion 44. Gas spring 40 is activated by depression of activation pin 42. When gas spring 40 is activated, the contents of pressurized cylinder portion 44 are either expelled or compressed. This action is used to raise or lower the height of the IV bag support 124. Gas spring 40 is available as Part Number KNOB-2-610-1295-100N from Easy Lift, Inc., 50 West Drive, Melborne, Fla. 32901. Gas spring 40 is more fully described at www.easyliftspring.com the entire web site of which is hereby incorporated by reference in its entirety into this specification. In the embodiment shown, gas spring 40 is vertically mounted with piston portion 44 pointing down and lower end portion 45 of piston portion 44 passing through an opening 36 (to be described) of a support plate 30 (to be described) and secured thereto by conventional means such as nuts secured to external threads (not shown) on the end portion 45. In the embodiment shown, gas spring 40 is capable of lifting about 30 lbs with minimal or no assistance. A different sized gas spring 40 may be used for lesser or greater loads. Gas spring 40 is also adjustable prior to assembly and can be pre-configured for use in specific locations, depending on quantity/weight of fluids to be elevated.

Support plate 30 comprises a lower surface 32, an upper surface 34, a centrally disposed opening 36, clearance holes 38, and threaded mounting holes 39. Upon assembly of gas spring 40 and support plate 30, actuation pin 42 passes or extends thru centrally disposed opening 36. As will be described more fully herein, mounting holes 38 are adapted to securely connect outerpost support 82 to support plate 30. Support plate 30 may be made from conventional materials such as steel.

Extension arm 74 generally comprises a lower end portion 76, an upper portion 78, and an upper end portion 80. Lower end portion 76 is securely connected to cylinder portion 46 by conventional means such as a screw and internal threads. Extension arm 74 may be made from conventional materials such as steel tubing.

Figure 6:
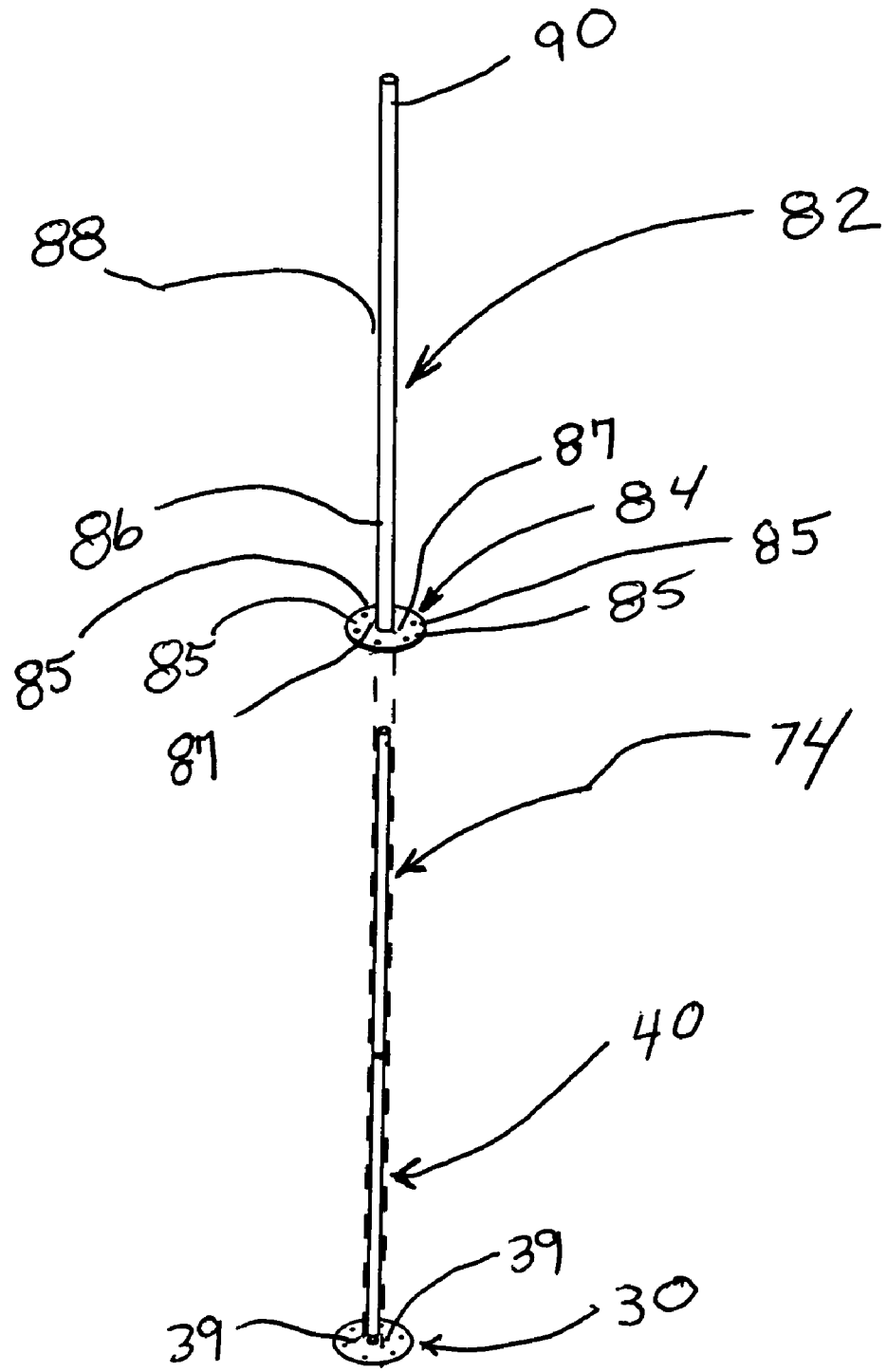
FIG. 6 is an exploded view showing the outer post support member and the gas spring.

Referring to FIG. 6, gas spring 40 and extension arm 72 are substantially enclosed by outer post support 82. Outer post support 82 generally comprises a base portion 84 having mounting holes 85 and 87 and an elongated hollow body portion 86 having a median portion 88 and an upper end portion 90. Outer post support 82 is adapted to slide over extension arm 74 and gas spring 40 and the base portion 84 is connected to support plate 30 by securing mounting holes 87 of base portion 84 with mounting holes 39 of support plate 30 by conventional means such as screw. Outer post support 82 may be made from conventional materials and processes. In the embodiment shown, base portion 84 takes the form of a circular plate made from steel which is welded to hollow body portion 86. Hollow body portion 86 is made from steel tubing. Outer post support 82, support plate 30, gas spring 40, and extension arm 74 form a single assembly that is mounted to base member 14. Outer post support 82, support plate 30, gas spring 40, and extension arm 74 are assembled as a single unit and connected to base member 14 by securing mounting holes 85 of base portion 84 with mounting holes 22 of the base member 14 by conventional means such as bolts and nuts. The bolts pass thru clearance holes 38 of support plate 30.

Figure 7:
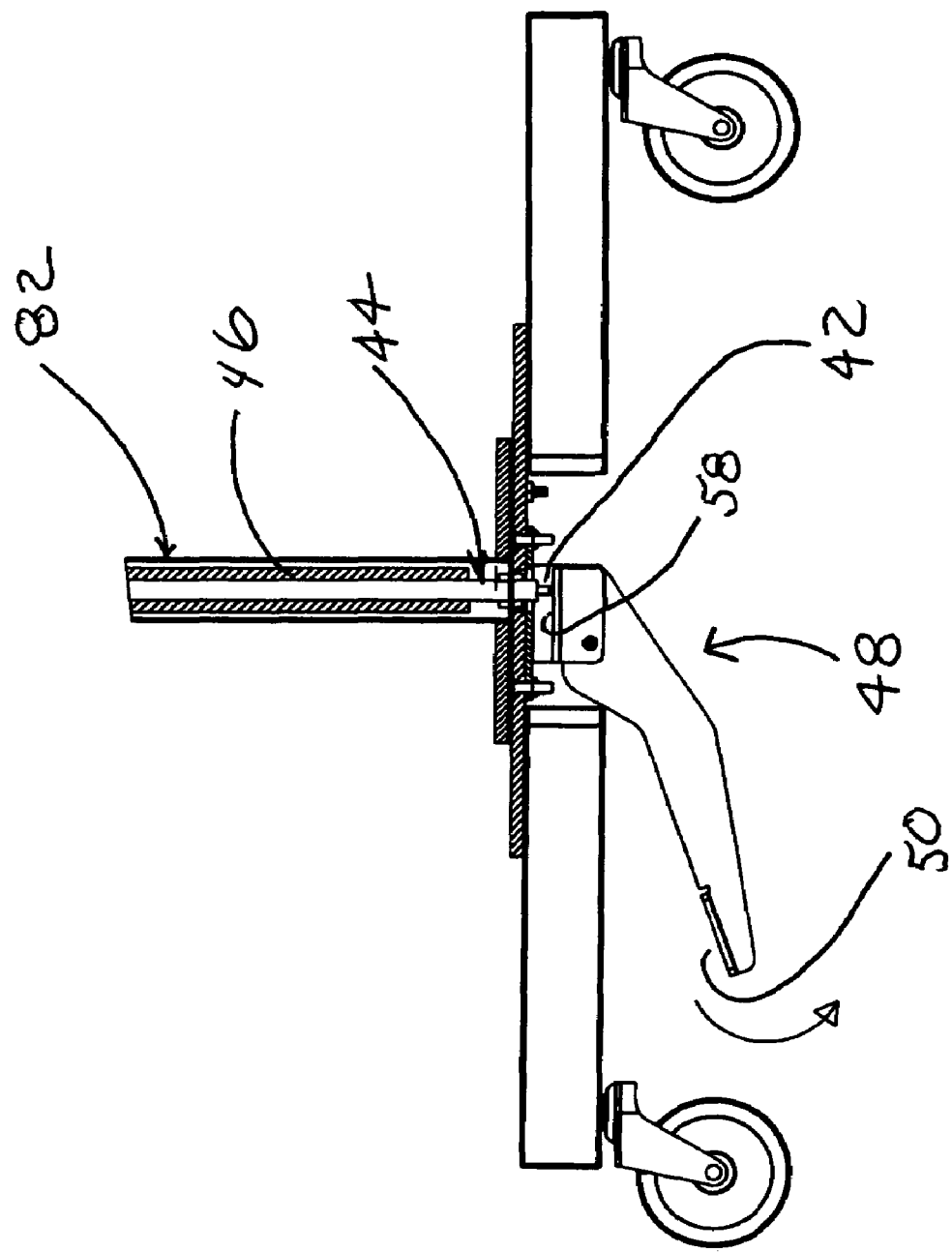
FIGS. 7 and 8 are cross section views showing the foot pedal engaged with an actuation pin of the gas spring.
Figure 8:
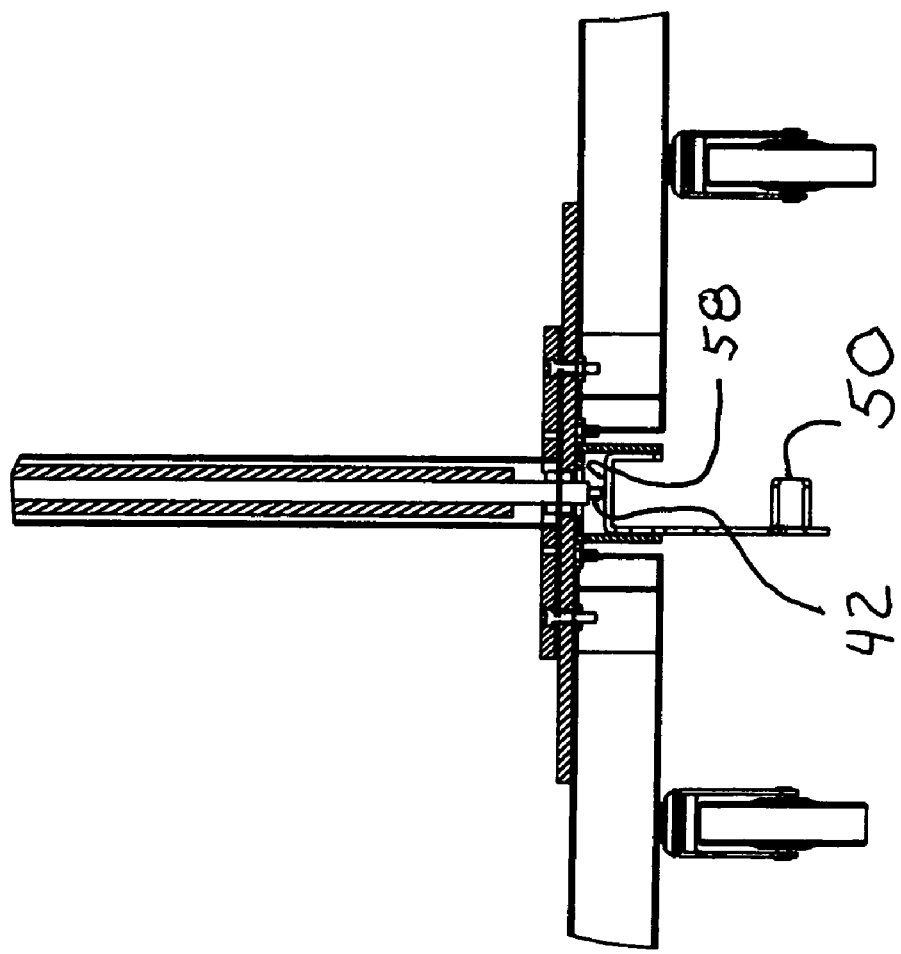

Referring to FIGS. 7-8, foot pedal assembly 48 is shown connected to base member 14 with engagement surface 58 in direct contact with actuation pin 42 of gas spring 40. Depression of front portion 52 of foot pedal 50 causes engagement surface 48 to depress activation pin 42 and activate gas spring 40. Release of front portion 52 causes activation pin 42 to return to its normally biased outward position and turning off gas spring 40 and fixing the position of the cylinder portion 44 and therefore the height of extension arm 74 and IV bag support 124.

Figure 9:
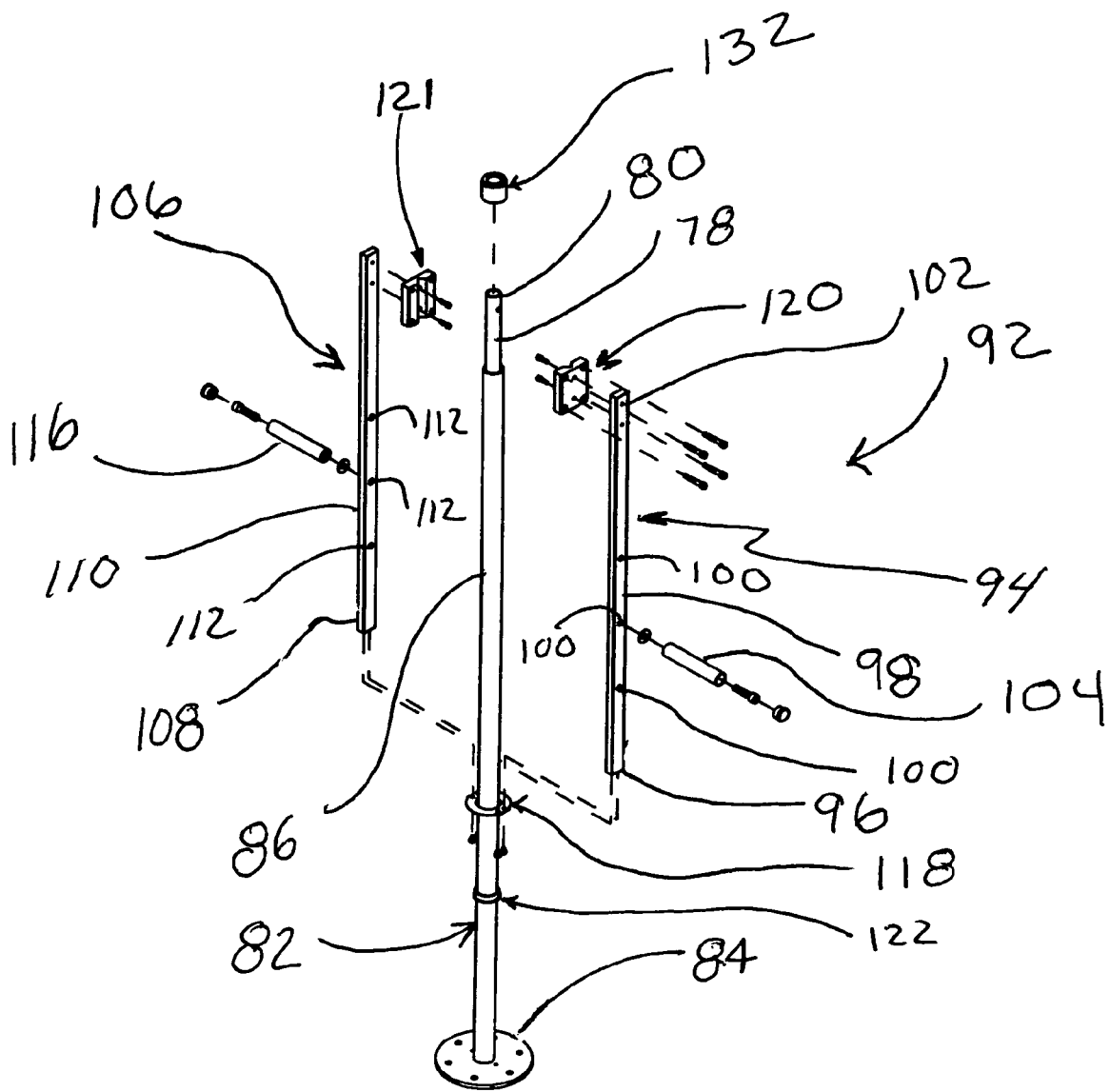
FIG. 9 is an exploded view of the handle assembly securely mounted to the extension arm and slidably moveable along the outer post support.

Referring to FIG. 9, handle assembly 92 generally comprises first and second rectangular shaped and vertically disposed support members 94 and 106 securely connected to upper portion 78 of extension arm 74 by a pair of upper mounting members 120 and 121. In the embodiment shown, upper mounting members 120 and 121 may take the form of clamps securely fastened together about extension arm 74 by conventional means. First support member 94 generally comprises a lower portion 96, a median portion 98 having a plurality of evenly spaced threaded holes 100, and an upper portion 102. Upper portion 102 is securely connected to upper mounting member 120 by conventional means. Similarly, second support member 106 generally comprises a lower portion 108, a median portion 110 having a plurality of evenly spaced threaded holes 112, and an upper portion 114. Upper portion 114 is securely connected to upper mounting member 121 by conventional means. First and second support members 94 and 106 may be made from aluminum bar stock by conventional processes. Handle assembly 92 may further comprise a first hand grip portion 104 connected to first support member 94 at one of openings 100 by conventional means such as a screw. Handle assembly 92 may further comprise a second hand grip portion 116 connected to second support member 106 at one of openings 112 by conventional means such as a screw. Hand grip portions 104 and 116 are height adjustable to meet the ergonomic needs of individual operators. First and second hand grip portions 104 and 116 and first and second vertical support members 94 and 106 are disposed on opposite sides of outer post support 82 to provide a means of applying even during downward movement of extension arm 74 and therefore cylinder portion 46.

Lower portions 96 and 108 of the first and second support members 94 and 106, respectively, are securely connected to a lower handle support 118. In the embodiment shown, lower handle support 118 is a round piece of metal stock having a larger diameter than the outer post support 82 and travels freely/vertically over the outer post support 82. Lower handle support 118 may be guided by a plastic bushing 122. An upper bushing 132 may be provided to slidably support the upper end portion 80 of the extension arm within the outer post support 82.

Figure 10:
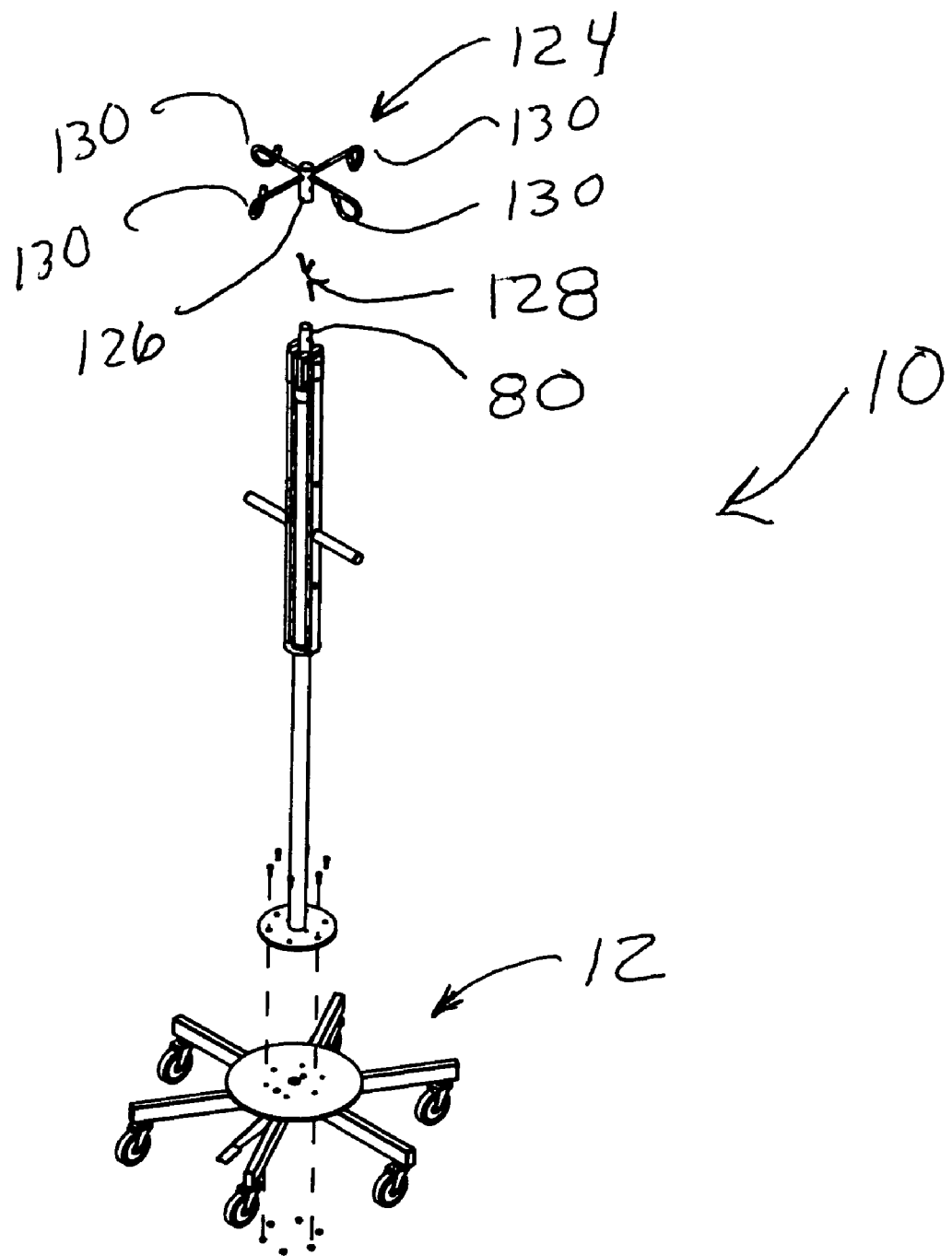
FIG. 10 is an exploded view of the infusion stand showing the IV bag support securely connected to the upper end portion of the extension arm.

Referring to FIG. 10, IV bag support 124 comprises a tubular base portion 126 securely connected to upper end portion 80 of extension arm 74 by conventional means such as spring clip 128. IV bag support 124 further comprises a plurality of ram hooks 130 adapted to support conventional IV/irrigation fluid bags 8 and/or bottles. In the embodiment shown, the infusion stand 10 may have about up to 12,000 ml of intravenous and/or irrigation solutions suspended from ram hooks 126. Tubular base portion 126 and ram hooks 130 may be from conventional materials and processes.

To elevate the IV bag 8, an operator merely depresses the foot pedal 50 and the IV bags 8 are raised with no upper body power or at most slight upward finger pressure of one hand. Lowering the bag 8 is achieved by depressing the foot pedal 50 and if necessary, applying downward pressure on one or both of hand grip portions 104 and 116. Vertically disposed support members 94 and 106 and/or grip portions 104 and 106 allow the operator to control upward or downward movement of IV bag support 124 while the foot pedal 50 is depressed and fix the desired height by release of foot pedal 50. The amount of pressure required by operator is directly dependent on the weight of fluid suspended from the ram hooks 126.

The foregoing description is intended primarily for purposes of illustration. This invention may be embodied in other forms or carried out in other ways without departing from the spirit or scope of the invention. Modifications and variations still falling within the spirit or the scope of the invention will be readily apparent to those of skill in the art.

What is claimed:

1. An infusion stand for supporting an IV bag comprising:
a base member comprising a centrally disposed opening;
a gas spring comprising an actuation pin extending thru said centrally disposed opening;
an extension arm comprising a lower end portion engaged with said gas spring and an upper end portion;
at least one support hook engaged with said extension arm;
a foot pedal engaged with said base and said actuation pin of said gas spring; depression of said foot pedal causes depression of said actuation pin and movement of said extension arm;
an outer post support substantially disposed about said gas spring and said lower end portion of said extension arm; said outer post support comprising a lower end portion engaged with said base and an upper end portion; said upper end portion of said extension arm extending outward from said upper end portion of said outer post support; and
a handle assembly comprising first and second elongated supports each having lower and upper end portions; said handle assembly further comprising first and second clamps secured to said upper end portion of said extension arm; said upper end portions of said first and second elongated supports are connected to said first and second clamps, respectively; said handle assembly further comprising a lower handle support disposed about and freely movable along said outer post support with said movement of said extension arm; said lower end portions of said first and second elongated supports are connected to said lower handle support; said first and second elongated supports are substantially parallel to said extension arm and said outer post support; said handle assembly further comprising first and second handles engaged with said first and second elongated supports, respectively.

2. The device of claim 1, wherein said first clamp is connected to said second clamp about said upper end portion of said extension arm.

3. The device of claim 1, wherein said handle assembly further comprises a bushing disposed between said lower handle support and said outer post support.

4. The device of claim 3, wherein said lower handle support is round and has a diameter larger than said outer support post.

5. The device of claim 4, wherein said lower handle support is made from metal and said bushing is made from plastic.

6. The device of claim 5, wherein said first and second handles are substantially perpendicular to said first and second elongated supports, respectively.

7. The infusion stand of claim 6, further comprising a support plate having an inner surface, an outer surface, and a centrally disposed opening.

8. The infusion stand of claim 7, wherein said gas spring is engaged with said support plate and said actuation pin passes thru said centrally disposed opening of said support plate and said centrally disposed opening of said base member.

9. The infusion stand of claim 8, wherein said outer post support comprises a base portion connected to said inner surface of said support plate.

10. The infusion stand of claim 9, wherein said outer surface of said support plate is connected to said base member.

11. The device of claim 10, further comprising four IV support hooks.

\* \* \* \* \*